United States Patent
Ridenour et al.

(10) Patent No.: US 10,788,522 B1
(45) Date of Patent: Sep. 29, 2020

(54) NON-CONTACT, CAPACITIVE, PORTABLE PRESENCE SENSING

(71) Applicants: Samuel Alden Ridenour, Saint Charles, IL (US); Paul Michael Wempe, Saint Charles, IL (US); Mark Andrew Hanson, Fairfax, VA (US); Adam T. Barth, Annandale, VA (US)

(72) Inventors: Samuel Alden Ridenour, Saint Charles, IL (US); Paul Michael Wempe, Saint Charles, IL (US); Mark Andrew Hanson, Fairfax, VA (US); Adam T. Barth, Annandale, VA (US)

(*) Notice: Subject to any disclaimer, the term of this patent is extended or adjusted under 35 U.S.C. 154(b) by 290 days.

(21) Appl. No.: 15/942,784

(22) Filed: Apr. 2, 2018

Related U.S. Application Data

(63) Continuation of application No. 13/828,847, filed on Mar. 14, 2013, now Pat. No. 9,933,469.

(60) Provisional application No. 61/728,008, filed on Nov. 19, 2012.

(51) Int. Cl.
 *G01R 27/26* (2006.01)

(52) U.S. Cl.
 CPC .............................. *G01R 27/2605* (2013.01)

(58) Field of Classification Search
 CPC ................................................ G01R 27/2605
 See application file for complete search history.

(56) References Cited

U.S. PATENT DOCUMENTS

| | | | |
|---|---|---|---|
| 4,320,766 A | 3/1982 | Alihanka | |
| 6,006,386 A | 12/1999 | Mohaupt | |
| 6,033,370 A | 3/2000 | Reinbold | |
| 6,499,359 B1 | 12/2002 | Washeleski | |
| 7,578,195 B2 | 8/2009 | DeAngelis | |
| 7,719,007 B2 | 5/2010 | Tompkins | |
| 8,598,893 B2 | 12/2013 | Camus | |
| 8,919,211 B1 | 12/2014 | Hanson | |

(Continued)

OTHER PUBLICATIONS

U.S. Non-Final Office Action for U.S. Appl. No. 13/828,330 dated May 9, 2014, 11 pages.

(Continued)

*Primary Examiner* — Manuel A Rivera Vargas
(74) *Attorney, Agent, or Firm* — Fish & Richardson P.C.

(57) ABSTRACT

A movement-sensitive capacitive sensor includes a first conductive element and a second conductive element positioned adjacent to the first conductive element. The sensor also includes a first protective insulator and a second protective insulator sealed to the first protective insulator with the first conductive element and the second conductive element positioned between the first protective insulator and the second protective insulator. The sensor further includes a circuit configured to calculate, over time while a person is occupying the movement-sensitive capacitive sensor and moving while occupying the movement-sensitive capacitive sensor, capacitance values between the first conductive element and the second conductive element. The circuit also is configured to determine an occupancy state of the movement-sensitive capacitive sensor based on the calculated capacitance values, determine movement-sensitive measurements based on the calculated capacitance values, and transmit output based on the determined occupancy state and the determined movement-sensitive measurements.

19 Claims, 9 Drawing Sheets

(56) References Cited

U.S. PATENT DOCUMENTS

2004/0017210 A1* 1/2004 Johnson ................ A61B 5/11
                                                  324/661
2004/0096368 A1   5/2004  Davis
2004/0240724 A1  12/2004  Fujii
2008/0136236 A1   6/2008  Kincaid
2010/0014101 A1   1/2010  Davidson

OTHER PUBLICATIONS

U.S. Notice of Allowance for U.S. Appl. No. 13/828,330 dated Aug. 15, 2014, 8 pages.
U.S. Non-Final Office Action for U.S. Appl. No. 14/584,621 dated Sep. 30, 2015, 16 pages.
U.S. Final Office Action for U.S. Appl. No. 14/584,621 dated Jun. 17, 2016, 8 pages.

* cited by examiner

NON-CONTACT, CAPACITIVE, PORTABLE PRESENCE SENSING

CROSS REFERENCE TO RELATED APPLICATIONS

This application is a continuation (and claims the benefit of priority under 35 USC 120) of U.S. application Ser. No. 13/828,847, filed Mar. 14, 2013, now allowed, which claims the benefit of U.S. Provisional Application Ser. No. 61/728,008, filed Nov. 19, 2012. Both of these prior applications are incorporated by reference in their entirety.

TECHNICAL FIELD

This disclosure relates to non-contact, capacitive, portable presence sensing.

BACKGROUND

Recent technological advancements have facilitated the detection of occupancy on human support surfaces such as beds, cushioned seats, and non-cushioned seats (e.g., chairs and sofas) via sensors placed directly above or below the support surface (e.g., cushion or mattress). More specifically, a binary occupancy sensor produces a distinct output when a support surface is either occupied or unoccupied. Beyond support surface detection, a broad application space exists for human-centric binary occupancy sensing, ranging from safety to wellness assessment. For example, bed and seat occupancy sensors can be utilized to measure and assess sedentary behavior (e.g., time spent in bed or seat) and fall risk (e.g., bed entries and exits, time spent away from bed, etc.). Occupancy can be measured with electrically conductive contacts (e.g., electrical contact created when occupied) or more complex sensing mechanics (e.g., resistive, load cell, pressure, etc.) filtered to produce binary output.

More complex sensing elements can also measure small variations in movement and provide corresponding variable output. Such sensors are typically placed in close proximity the sensed body. Combined with sophisticated signal filtering and processing, diverse applications of such movement-sensitive sensors range from sleep quality measurement to detection of breathing rate, heart rate, and sleep apnea.

SUMMARY

Techniques are described for non-contact, capacitive, portable presence sensing.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Techniques are described for non-contact, capacitive, portable bed and seat presence sensing. In some implementations, a sensor has adjacent capacitive sensing elements, combined with in-sensor computational processing, that allows for both binary occupancy detection and movement-sensitive variable measurement. In these implementations, the sensor may have a flexible and fabric structure that allows it to be utilized as an external sensor on existing beds and seats (e.g., above the surface and near the sensed body) or integrated into bed or seat constructions (e.g., within the bed or seat) without being felt by the user. The sensor may be inexpensive, hygienic, comfortable, accurate, precise, and/or portable (e.g., easily moved between application environments and support surfaces).

Figure 1:
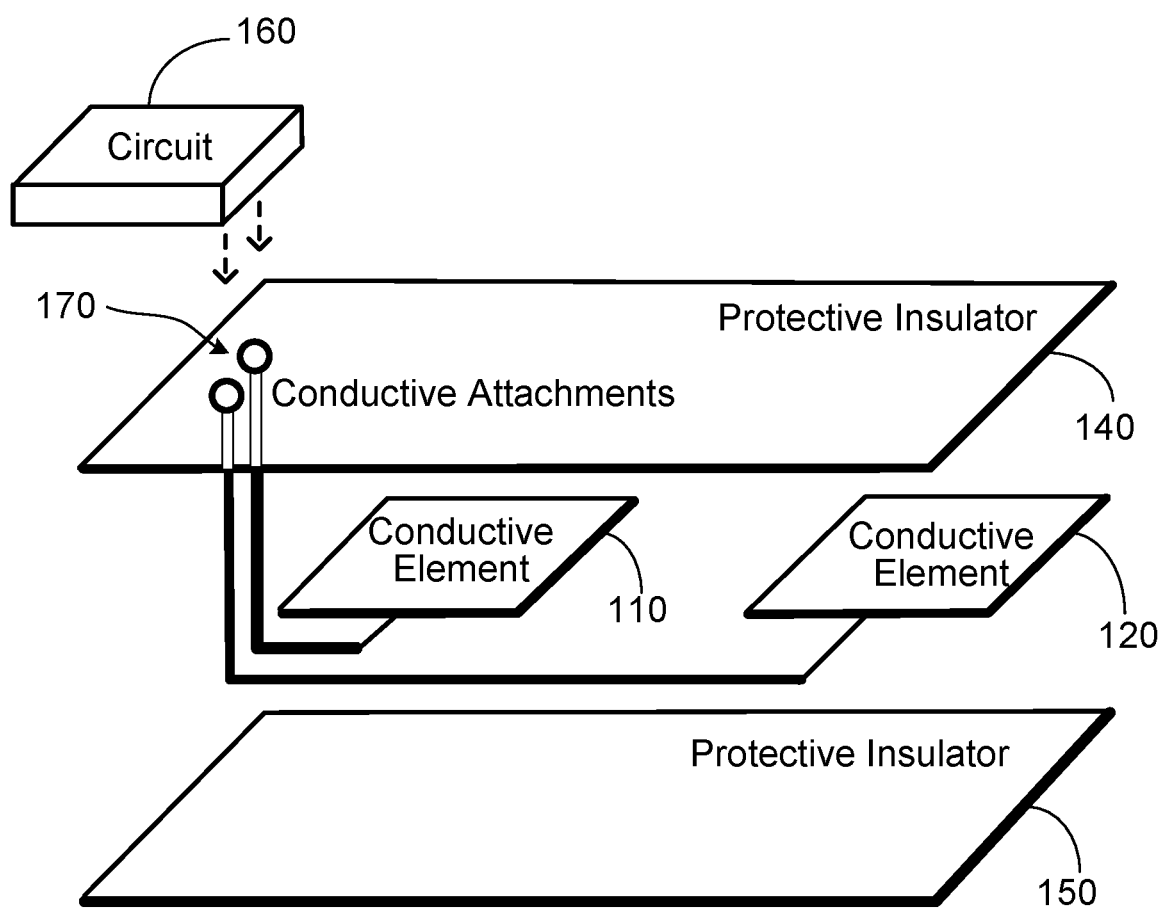
FIGS. 1 and 2 are diagrams that illustrate example capacitive sensors.

FIG. 1 illustrates an example capacitive sensor 100. The capacitive sensor 100 is a non-contact capacitive sensor that includes conductive elements 110 and 120. A top protective insulator 140 and a bottom protective insulator 150 are sealed together to encase the conductive elements 110 and 120. The top protective insulator 140 and the bottom protective insulator 150 may include anti-microbial surfaces, non-slip surfaces, or simple fabrics. The capacitive sensor 100 also includes a computational circuit 160 attached via wires and conductive attachment points 170 to the conductive elements 110 and 120. The conductive attachment points 170 may include a conductive fastener, such as conductive Velcro, that provides a direct connection between the circuit 160 and the conductive elements 110 and 120.

Figure 2:
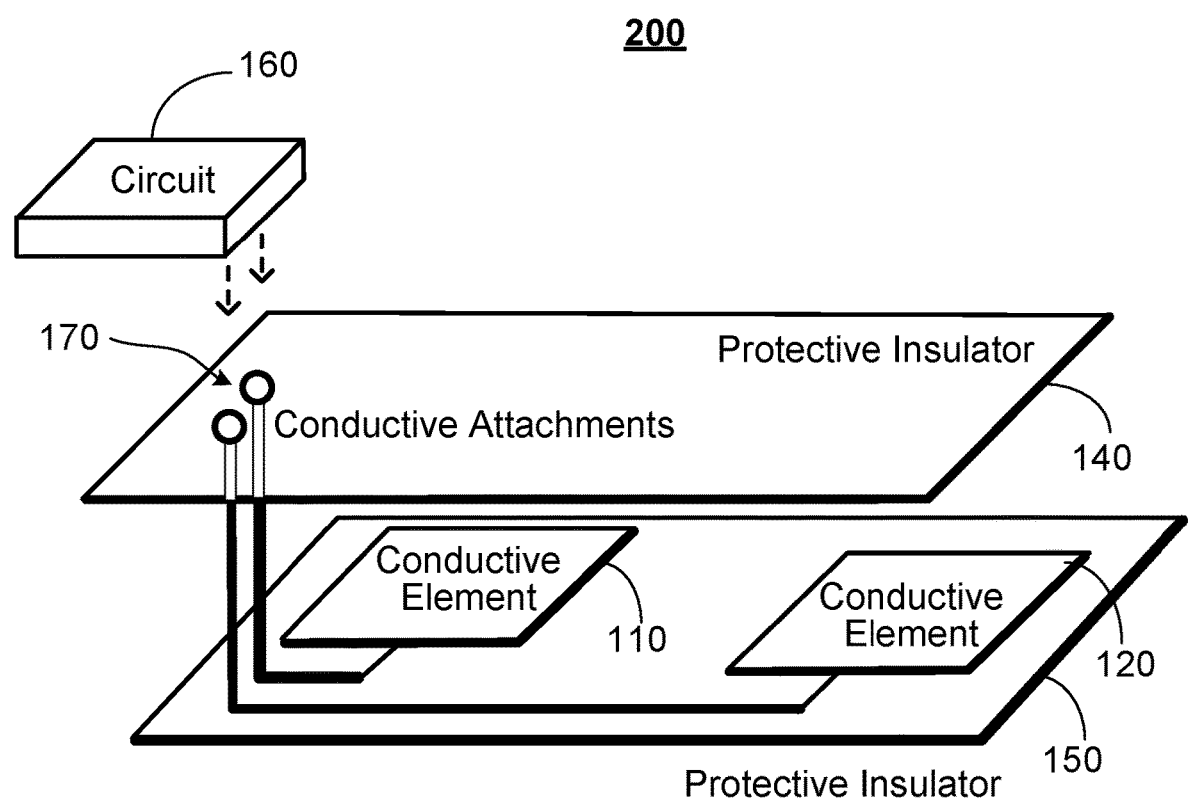

FIG. 2 illustrates another example capacitive sensor 200. In the capacitive sensor 200, the conductive elements 110 and 120 are printed on or adhered to the bottom protective insulator 150. In other implementations, the conductive elements 110 and 120 may be printed on or adhered to the top protective insulator 140. The conductive elements 110 and 120 may be conductive ink printed on the top protective insulator 140 or the bottom protective insulator 150.

Figure 3:
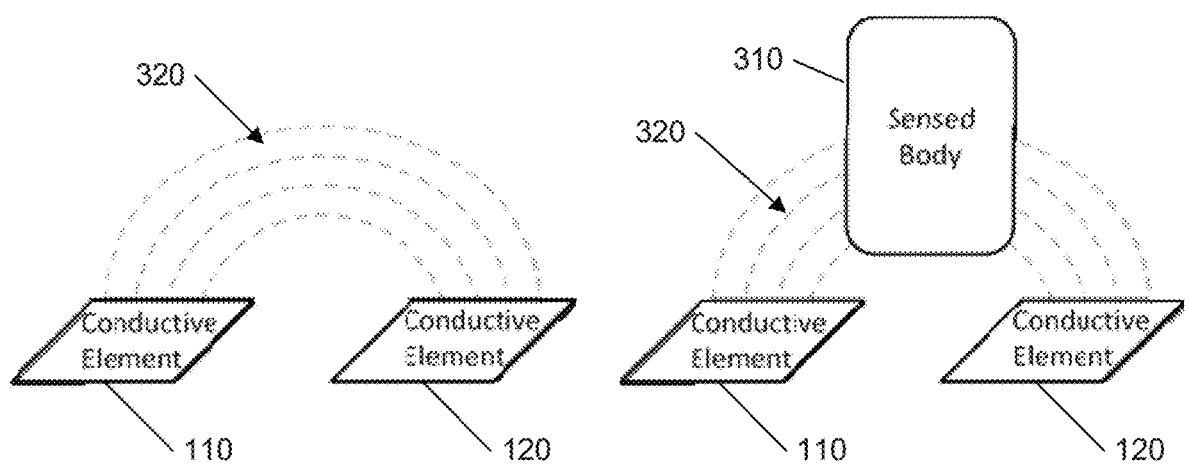
FIG. 3 is a diagram that illustrates the capacitive sensing principle.

As shown in FIG. 3, in the capacitive sensor 100 as shown in FIG. 1 and the capacitive sensor 200 as shown in FIG. 2, the conductive elements 110 and 120 are placed adjacent to one another to define a capacitive element influenced by presence of a sensed body within close proximity. When a sensed object 310, such as a human body, is near the conductive elements 110 and 120, electric field lines 320 between the conductive elements are disrupted, and the charge distribution on the conductive elements 110 and 120 changes. The left portion of FIG. 3 shows the electric field lines 320 undisrupted and the right portion of FIG. 3 shows the electric field lines 320 disrupted by the sensed object 310. The circuit 160 detects the change in charge distribution on the conductive elements 110 and 120 to sense the presence of the sensed object 310.

Figure 4:
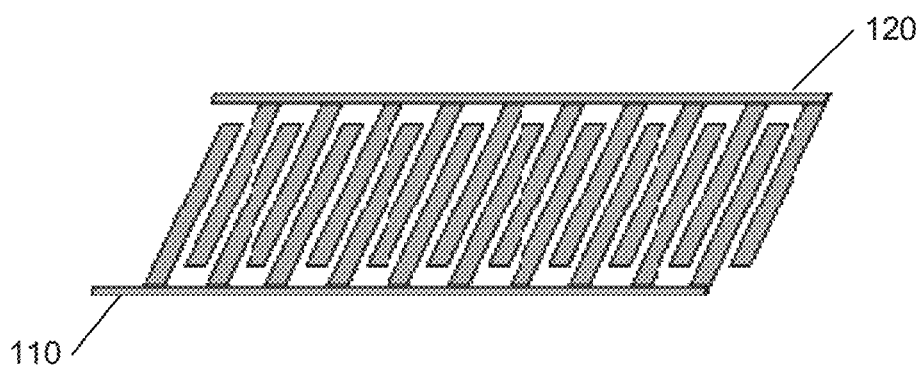
FIG. 4 is a diagram that illustrates an example interlocking comb-tooth conductive element pattern.

In some examples, the conductive elements 110 and 120 may be patterned to increase sensitivity to movement of the sensed body and/or to increase sensitivity of sensing position of the sensed body relative to the sensor. FIG. 4 illustrates an example interlocking comb-tooth conductive element pattern for the conductive elements 110 and 120. The interlocking comb-tooth conductive element pattern may be used to increase sensitivity to movement on the surface of the sensor. In this example, the two conductive elements 110 and 120 are shaped to increase the detection area and/or to identify the area of the body in contact with the sensor.

Figure 5:
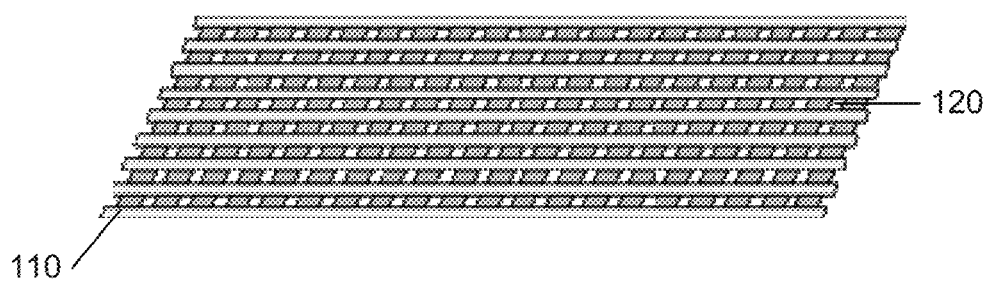
FIG. 5 is a diagram that illustrates an example cross-bar array conductive element pattern.

FIG. 5 illustrates an example cross-bar array conductive element pattern for the conductive elements 110 and 120. The cross-bar array may be used to identify position of the sensed body relative to the sensing surface. In this example, a multiplicity of conductive elements provides a grid from which adjacent elements may be measured to determine position in the sensing plane (e.g., two-axes of position). The grid may include a separate conductive element for each row and each column such that changes in charge distribution on adjacent conductive elements may be measured to identify a two-dimensional location at each point where the body contacts or is positioned over the sensor.

Figure 6:
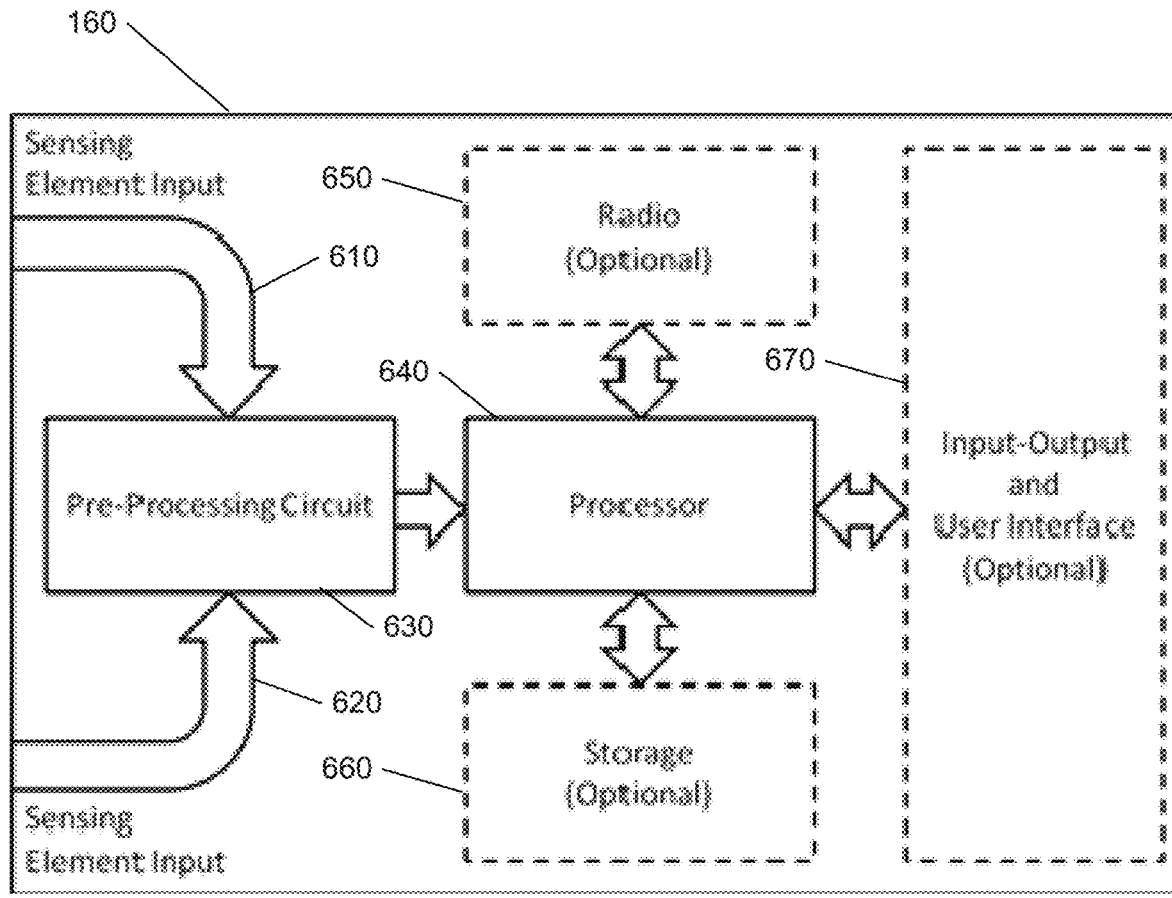
FIG. 6 is a diagram that illustrates an example circuit.

FIG. 6 illustrates an example of the circuit 160. As shown in FIG. 6, the circuit 160 includes digital and analog components that convert capacitance to a digital value. For instance, the circuit 160 includes a first sensing element input 610 that is connected to the conductive element 110 and a second sensing element input 620 that is connected to the conductive element 120. The circuit 160 also includes a pre-processing circuit 630 and a processor 640. In some implementations, the pre-processing circuit 630 may also be integrated into the processor 640. The pre-processing circuit 630 receives input from the first sensing element input 610 and from the second sensing element input 620 and performs pre-processing on the received inputs. The pre-processing circuit 630 provides results of pre-processing to the processor 640. The pre-processing circuit 630 and processor 640 digitally process the signals for the conductive elements to detect occupancy or quantify small changes in movement of the sensed body. For example, the pre-processing circuit 630 may convert sensed capacitance between the conductive elements 110 and 120 into an oscillating signal of varying frequency at digital logic levels.

Moreover, the circuit 160 may include a wireless radio 650 that transmits capacitance, occupancy, or small changes in the sensed body's movement to a remote location (e.g., a base station, a mobile device, a wireless router, etc.). The circuit 160 also may include local memory/storage 660 that stores capacitance, occupancy, or movement data. The memory/storage 660 may temporarily store capacitance or occupancy data prior to transmission by the wireless radio 650 to a remote location (e.g., a base station, a mobile device, a wireless router, etc.). Further, the circuit 160 may include input/output and user interface components 670 (e.g., a button and a light-emitting diode (LED)) to facilitate user interaction. User interaction may be necessary for sensor calibration prior to use. For example, the circuit 160 may receive user input that initiates a calibration process and that indicates that no user is present on the sensing surface. In this example, the circuit 160 may measure the capacitance in the unoccupied state based on receiving the user input to calibrate the sensor. Calibration may promote higher accuracy measurement.

To measure capacitance, the circuit 160 may employ various processes. For example, the circuit 160 may utilize a Schmitt-trigger along with a resistor to oscillate between digital logic levels ("0" and "1") at a frequency directly related to the sensed capacitance and the "RC time constant" created with the added resistance. In this example, the oscillating signal serves as a clock source for a counter. The difference in counter value is measured over a known period of time (obtained from another time source), and the number in the counter directly corresponds to the sensed capacitance.

In another example, the circuit 160 measures capacitance by introducing a transient input in voltage and/or current and then measuring the response to the transient input with respect to time. In this example, the circuit 160 calculates capacitance based on the measured response and time. These processes, among others, may be used to sense minute changes in capacitance with small, inexpensive, and power efficient circuitry. The power efficiency may allow the circuit 160 to be externally or battery powered.

Figure 7:
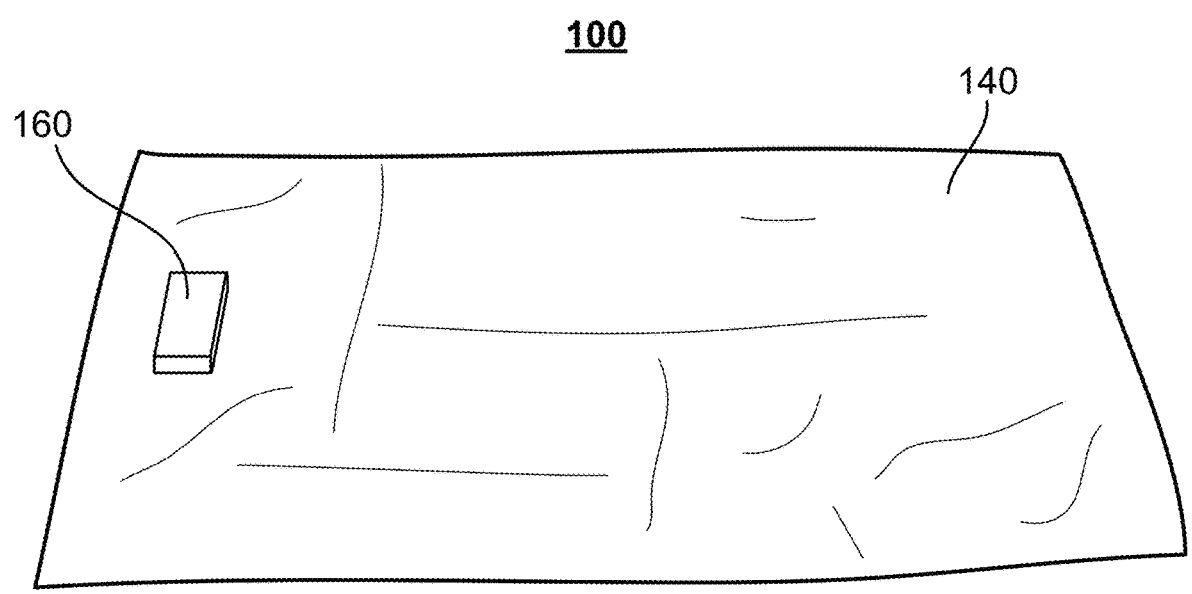
FIG. 7 is a view that illustrates an external appearance of an example capacitive sensor.

FIG. 7 illustrates an example implementation of the capacitive sensor 100 with a top view being shown. As shown in the top view, the top protective insulator 140 defines an external top surface of the capacitive sensor 100. The circuit 160 is positioned within a circuit box, which is external to the sensor protective insulators 140 and 150. Wires or a conductive fastener connect the circuit 160 to the conductive element 110 and the conductive element 120, which are positioned between and covered by the top protective insulator 140 and the bottom protective insulator 150.

Figure 8:
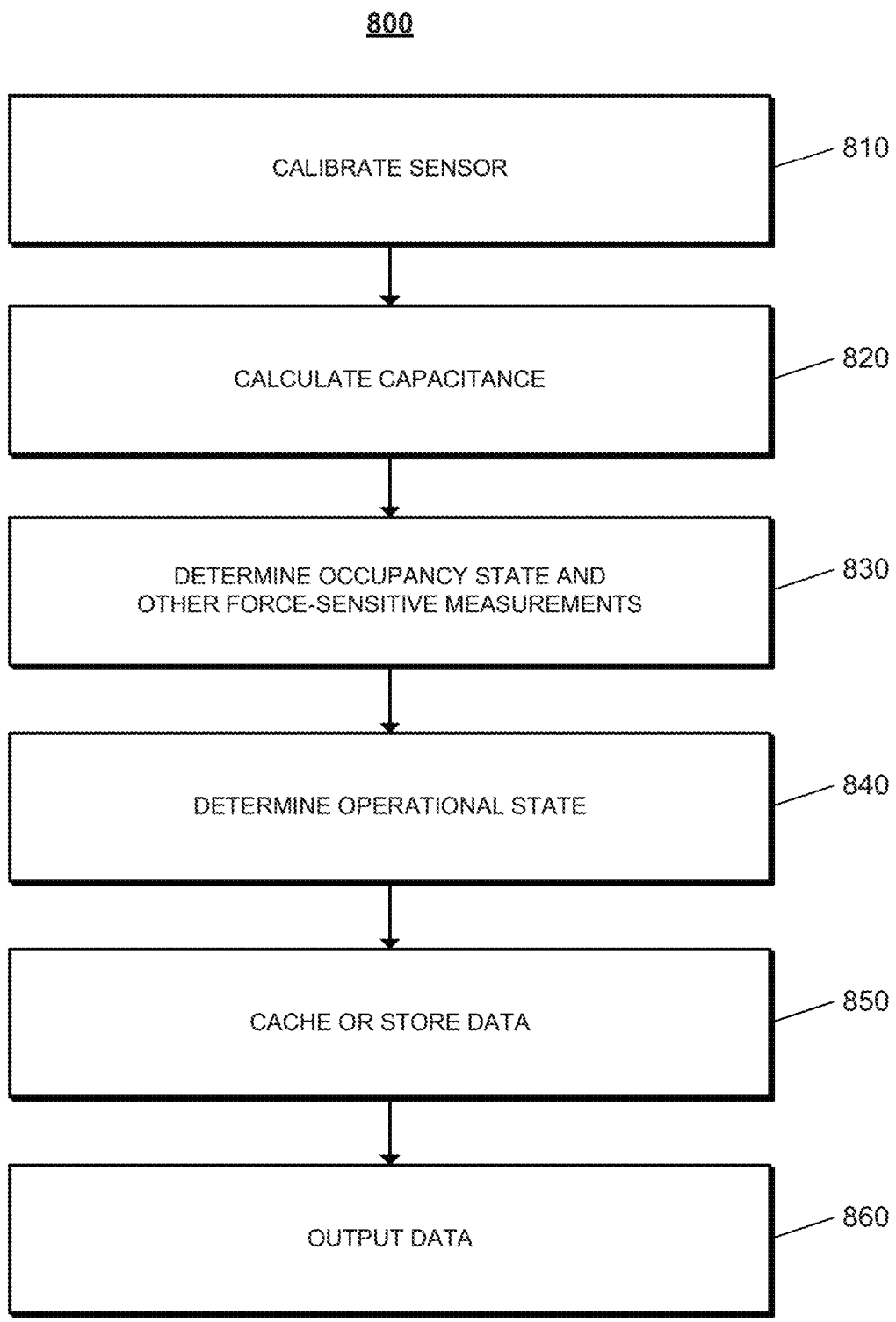
FIG. 8 is a flow chart illustrating an example process for occupancy sensing.

FIG. 8 illustrates an example process 800 for occupancy sensing. The operations of the example process 800 are described generally as being performed by the circuit 160. In some implementations, operations of the example process 800 may be performed by one or more processors included in one or more electronic devices. As shown in FIG. 8, the circuit 160 provides computational capabilities to calibrate the sensor (810), calculate capacitance (820), determine occupancy state or other movement-sensitive measures (830), determine operational state (840), cache or store data (850), and transmit data off of the sensor (e.g., wirelessly) (860).

The circuit 160 calibrates the sensor 100 (810). The sensor 100 may be calibrated manually or automatically. To calibrate the sensor 100 manually, the circuit 160 determines that the sensor 100 is unoccupied based on receiving user input (e.g., a press of a button on the computational circuit device) or based on receiving, from another electronic device, a signal that initiates a calibration process (e.g., a wirelessly received command). Upon initiation of the calibration process, the circuit 160 determines a capacitance measured by the circuit 160 in the unoccupied state and uses the determined capacitance as a baseline measurement for calibrating the sensor 100. The circuit 160 may set a threshold between the occupied and unoccupied states by adding an offset value, δ, from the calibrated value. The offset value, δ, reduces the likelihood of minor environmental changes and electrical noise causing unwanted state transitions. Sensor calibration may be performed periodically, as the unoccupied capacitance value may change over time.

In some implementations, the circuit 160 may automatically perform periodic calibration without requiring user input or an outside signal to initiate the calibration. To calibrate the sensor automatically, the circuit 160 determines the unoccupied state and occupied state based on large rapid changes in the calculated capacitance values. To achieve this automatic calibration, the circuit 160 performs a process to manage these state changes.

Figure 9:
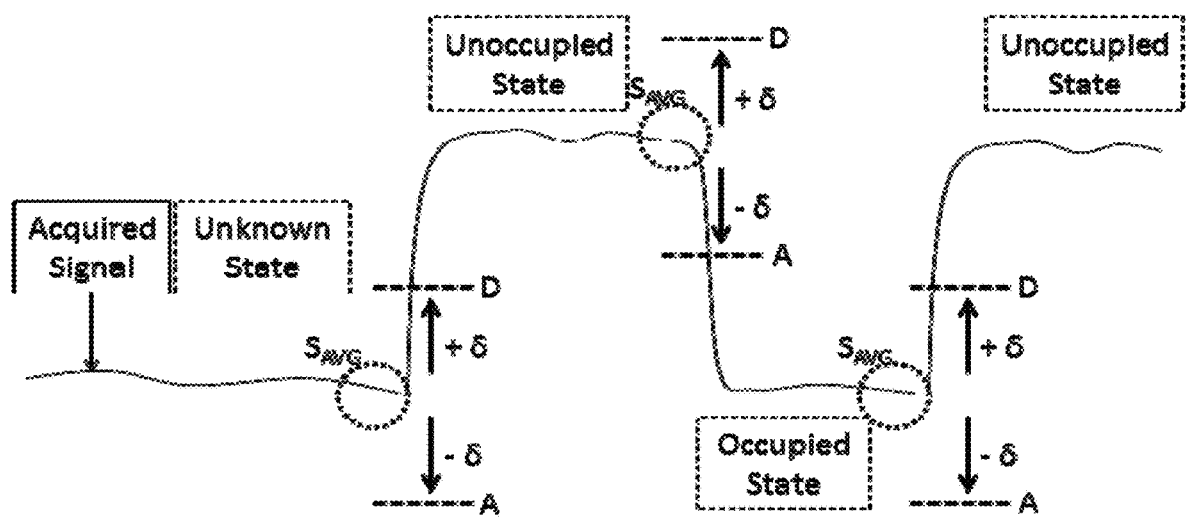
FIG. 9 illustrates an example signal corresponding to a transition to, and back from, an unoccupied state.

An example of an automatic calibration process is explained hereafter. FIG. 9 illustrates and annotates relevant variables for an example signal corresponding to a transition to, and back from, an unoccupied state. Sampled values corresponding to the current state are averaged over a multiplicity of samples (denoted as T) to subtract small changes in the applied dielectric, as well as noise from both the electrical and mechanical systems. Therefore, at any time t, the process has an estimate of the average acquired signal in the current state ($S_{AVG}$). Another variable, δ, is defined as the amount of signal change required for activation or deactivation. Activation and deactivation thresholds A and D are set as described in Eq. 1 and Eq. 2 (below). Consequently, the activation and deactivation thresholds are updated on the time interval, T, to compensate for small changes in the applied dielectric, and therefore, sensed capacitance corresponding to the unoccupied or occupied state.

$$A = S_{AVG} - \delta \qquad \text{Eq. 1: Activation Threshold Equation}$$

$$D = S_{AVG} + \delta \qquad \text{Eq. 2: Deactivation Threshold Equation}$$

Figure 10:
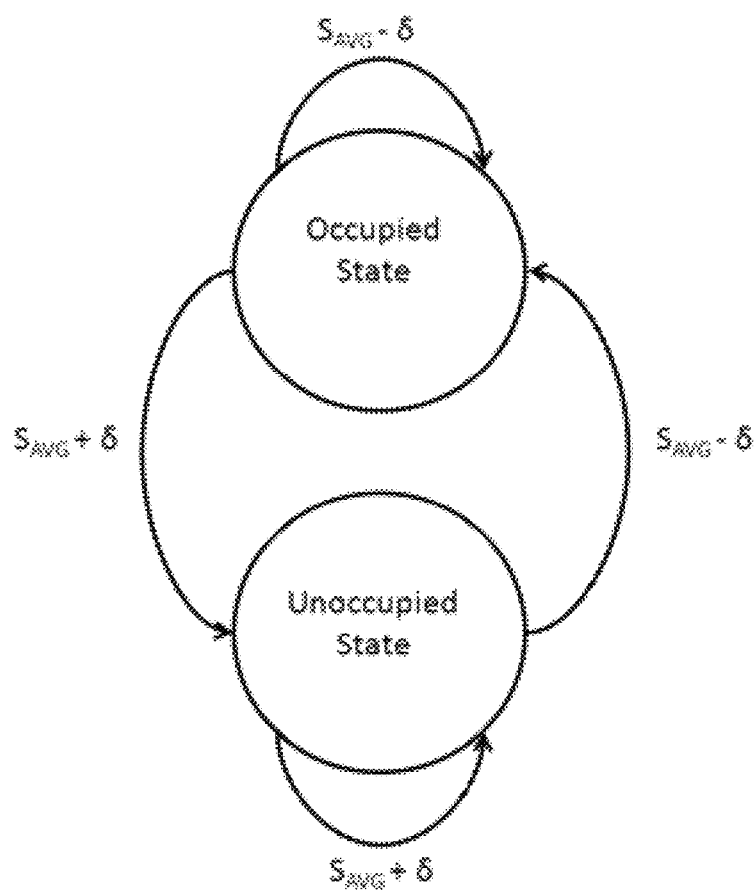
FIG. 10 illustrates an example state diagram that shows transitions from an occupied state to an unoccupied state and transitions necessary for auto-correction of state.

Without complete certainty of being in the correct state at any given time, it is possible that either an activation threshold or deactivation threshold is reached at any point in time, regardless of the current state. Accordingly, the approach for automatic calibration allows for auto-correction if the previous state was incorrect. FIG. 10 illustrates an example State Diagram 1000 that shows the transitions from the occupied state to the unoccupied state and the transitions necessary for auto-correction of state. If the system is incorrectly in the occupied state, then a capacitance change of −δ results in no state change and the resetting of $S_{avg}$ (the converse is true for the unoccupied state). The uncertainty of being in the incorrect state may be reduced by setting the offset variable, δ, to a large enough value so that it does not cause transitions based on minor environmental changes and electrical noise. Nonetheless, this offset variable, δ, needs to be small enough to accurately detect the presence of the desired object (e.g., the human body).

Other processes of automatic calibration also may be employed without the use of manual or command-initiated device input. For example, capacitance values may be statistically profiled and unsupervised machine learning processes may be implemented to classify occupancy state.

Referring again to FIG. 8, after the sensor 100 has been calibrated, the circuit 160 calculates capacitance (820). To measure capacitance, the circuit 160 may employ various processes. For example, the circuit 160 may utilize a Schmitt-trigger along with a resistor to oscillate between digital logic levels ("0" and "1") at a frequency directly related to the sensed capacitance and the "RC time constant" created with the added resistance. In this example, the oscillating signal serves as a clock source for a counter. The difference in counter value is measured over a known period of time (obtained from another time source), and the number in the counter directly corresponds to the sensed capacitance.

In another example, the circuit 160 measures capacitance by introducing a transient input in voltage and/or current and then measuring the response to the transient input with respect to time. In this example, the circuit 160 calculates capacitance based on the measured response and time.

The circuit 160 may calculate a change in capacitance by computing a difference between the measured capacitance and the baseline capacitance measured during calibration. The circuit 160 may use the change in capacitance to measure the movement of the sensed body near the sensor 100.

After the circuit 160 calculates capacitance, the circuit 160 determines an occupancy state and other movement-sensitive measurements (830). For instance, the circuit 160 may determine a binary occupancy state (e.g., occupied or not occupied) based on the calculated capacitance and also may determine high precision, movement-sensitive measurements based on the calculated capacitance. The circuit 160 may determine the high precision, movement-sensitive measurements by translating the calculated capacitance to movement of the sensed body proximal to the sensor 100. The sensed movement may be processed to extract properties of the sensed body such as breathing rate, sleep apnea, heart rate, or restlessness. The circuit 160 may calculate the movement-specific parameters on the processor 640.

The circuit 160 may use various processes to determine the binary occupancy state. For instance, the circuit 160 may detect occupancy based on measuring a capacitance greater than a threshold and detect a lack of occupancy based on measuring a capacitance less than the threshold. To reduce false activations or deactivations, the circuit 160 may use the activation and deactivation thresholds described above to manage small variations.

In addition to binary occupancy state, the circuit 160 may determine a location of sensed objects relative to the sensor. In the implementation shown in FIG. 5 in which the sensor includes a cross-bar array conductive element pattern, the circuit 160 may determine an occupancy state applied at each row and column intersection across the sensor. In this regard, the circuit 160 may determine a two-dimensional grid that represents occupancy state throughout the sensor for each frame. With the two-dimensional grid, the circuit 160 may detect which location of the sensor is being interacted with and monitor how that location changes over time.

The circuit 160 determines operational state of various components of the sensor 100 (840). For instance, the circuit 160 may determine a battery state of the circuit 160 battery. The circuit 160 also may detect when various trouble conditions arise within the sensor 100 (e.g., a connection to a conductive element of the sensor is lost). The circuit 160 may determine any measurable operational state of any of the components of the sensor 100 or circuit 160 and use the one or more measured operational states to proactively address any detected trouble conditions or to attempt prevention of trouble conditions before they arise.

The circuit 160 caches or stores data (850). For instance, the circuit 160 may store values related to the calibration process, in addition to state variables describing the sensor's operation state (e.g., battery state, trouble conditions, etc.). The circuit 160 also may store measured capacitance values, determined occupancy states, and/or other movement-specific measurements. The circuit 160 may store any data measured or determined by the circuit 160. The storage may be temporary and deleted after the data is transmitted to an external device.

The circuit 160 outputs data from the sensor 100 (860). For example, the circuit 160 may communicate to a user or transmit to an external device values related to the calibration process, in addition to state variables describing the sensor's or circuit's operation state (e.g., battery state, trouble conditions, etc.). The circuit 160 also may communicate to a user or transmit to an external device measured capacitance values, determined occupancy states, and/or other movement-specific measurements. The circuit 160 may continuously or periodically transmit data collected by the circuit 160. In some examples, the circuit 160 may delay transmission until the storage on the circuit 160 is nearly full (e.g., within a threshold storage amount of being full) and then transmit all of the stored data. In addition, the circuit 160 may transmit data upon request or may have rules that define when data should be transmitted based on the values measured. For instance, the circuit 160 may transmit data to indicate a measured capacitance above a threshold value, a determined change in occupancy state, or a particular occupancy state that lasts more than a threshold period of time. Any rules may be set to determine when the circuit 160 transmits data and what data the circuit 160 transmits. For example, the circuit 160 may predict occupancy states and only transmit measured occupancy states that differ from predicted states.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:
1. A movement-sensitive capacitive sensor comprising:
   a first conductive element;
   a second conductive element positioned adjacent to the first conductive element to define a capacitive structure influenced by a sensed body within close proximity of the first conductive element and the second conductive element;
   a first protective insulator;
   a second protective insulator sealed to the first protective insulator with the first conductive element and the second conductive element positioned between the first protective insulator and the second protective insulator; and
   a circuit connected to the first conductive element and the second conductive element, the circuit being configured to:
      calculate, over time while a person is occupying the movement-sensitive capacitive sensor and moving while occupying the movement-sensitive capacitive sensor, capacitance values between the first conductive element and the second conductive element,
      determining an average acquired signal in a current state by averaging, over a number of samples, values of measured capacitance between the first conductive element and the second conductive element;
      setting an activation threshold based on the average acquired signal in the current
      state and a value that defines an amount of signal change required for activation;
      setting a deactivation threshold based on the average acquired signal in the current state and a value that defines an amount of signal change required for deactivation;
      after setting the activation threshold and the deactivation threshold, monitoring a signal representative of measured capacitance between the first conductive element and the second conductive element with respect to the activation threshold and the deactivation threshold;
      based on the monitoring, determining that the signal representative of measured capacitance between the first conductive element and the second conductive element has crossed the activation threshold;
      based on the determination that the signal representative of measured capacitance between the first conductive element and the second conductive element has crossed the activation threshold, classifying the movement-sensitive capacitive sensor as in an occupied state; and
      transmit output that indicates that the movement-sensitive capacitive sensor is in an occupied state.

2. The movement-sensitive capacitive sensor of claim 1, wherein the movement-sensitive capacitive sensor has a flexible and fabric structure that allows it to be utilized as an external sensor on existing beds and seats.

3. The movement-sensitive capacitive sensor of claim 1, wherein the movement-sensitive capacitive sensor has a flexible and fabric structure that allows it to be integrated into a bed or seat construction.

4. The movement-sensitive capacitive sensor of claim 1, wherein the first conductive element and the second conductive element are patterned to increase sensing sensitivity.

5. The movement-sensitive capacitive sensor of claim 4, wherein the first conductive element and the second conductive element have an interlocking comb-tooth conductive element pattern that increases sensitivity to movement on a surface of the movement-sensitive capacitive sensor.

6. The movement-sensitive capacitive sensor of claim 4, wherein the first conductive element and the second conductive element have a cross-bar array conductive element pattern that enables identification of a two-dimensional position of the person on a surface of the movement-sensitive capacitive sensor.

7. The movement-sensitive capacitive sensor of claim 1, wherein the circuit is configured to determine the occupancy state of the movement-sensitive capacitive sensor by detecting occupancy based on calculating a capacitance value that is greater than a threshold and detecting a lack of occupancy based on calculating a capacitance value that is less than the threshold.

8. The movement-sensitive capacitive sensor of claim 1, wherein the circuit is configured to determine movement-sensitive measurements based on the calculated capacitance values by translating the calculated capacitance values to movement of the person proximal to the movement-sensitive capacitive sensor.

9. The movement-sensitive capacitive sensor of claim 1, wherein the circuit is further configured to determine the occupancy state of the movement-sensitive capacitive sensor by:
 based on detecting that the movement-sensitive capacitive sensor is in the occupied state, determining an average acquired signal in the occupied state by averaging, over the number of samples, values of measured capacitance between the first conductive element and the second conductive element;
 resetting the activation threshold based on the average acquired signal in the occupied state and the value that defines the amount of signal change required for activation;
 resetting the deactivation threshold based on the average acquired signal in the occupied state and the value that defines the amount of signal change required for deactivation;
 after resetting the activation threshold and the deactivation threshold, monitoring the signal representative of measured capacitance between the first conductive element and the second conductive element with respect to the reset activation threshold and the reset deactivation threshold;
 based on the monitoring, determining that the signal representative of measured capacitance between the first conductive element and the second conductive element has crossed the reset deactivation threshold; and
 based on the determination that the signal representative of measured capacitance between the first conductive element and the second conductive element has crossed the reset deactivation threshold, detecting that the movement-sensitive capacitive sensor is in an unoccupied state.

10. The movement-sensitive capacitive sensor of claim 1, wherein the circuit is further configured to determine the occupancy state of the movement-sensitive capacitive sensor by:
 based on detecting that the movement-sensitive capacitive sensor is in the occupied state, determining an average acquired signal in the occupied state by averaging, over the number of samples, values of measured capacitance between the first conductive element and the second conductive element;
 resetting the activation threshold based on the average acquired signal in the occupied state and the value that defines the amount of signal change required for activation;
 resetting the deactivation threshold based on the average acquired signal in the occupied state and the value that defines the amount of signal change required for deactivation;
 after resetting the activation threshold and the deactivation threshold, monitoring the signal representative of measured capacitance between the first conductive element and the second conductive element with respect to the reset activation threshold and the reset deactivation threshold;
 based on the monitoring, determining that the signal representative of measured capacitance between the first conductive element and the second conductive element has crossed the reset activation threshold; and
 based on the determination that the signal representative of measured capacitance between the first conductive element and the second conductive element has crossed the reset activation threshold, determining that the prior detection of the movement-sensitive capacitive sensor being in the occupied state was incorrect and that the movement-sensitive capacitive sensor is now in the occupied state.

11. The movement-sensitive capacitive sensor of claim 1, wherein the circuit comprises a wireless radio configured to transmit the output wirelessly to a remote location.

12. The movement-sensitive capacitive sensor of claim 1, wherein the circuit includes electronic storage configured to store data based on the determined occupancy state and the determined movement-sensitive measurements and the circuit is configured to transmit the output based on the data stored in the electronic storage.

13. The movement-sensitive capacitive sensor of claim 1, wherein the circuit is connected to the first conductive element and the second conductive element via conductive attachment points positioned on the first protective insulator.

14. The movement-sensitive capacitive sensor of claim 13, wherein the conductive attachment points include a first conductive fastener that provides a direct connection to the first conductive element and a second conductive fastener that provides a direct connection to the second conductive element.

15. The movement-sensitive capacitive sensor of claim 1, wherein the first protective insulator and the second protective insulator include anti-microbial fabrics and surfaces.

16. The movement-sensitive capacitive sensor of claim 1, wherein the first protective insulator and the second protective insulator include non-slip fabrics and surfaces.

17. The movement-sensitive capacitive sensor of claim 1, wherein the first conductive element and the second conductive element are separate structures from the first protective insulator and the second protective insulator and the second protective insulator is sealed to the first protective insulator to encase the first conductive element and the second conductive element.

18. The movement-sensitive capacitive sensor of claim 1, wherein the first conductive element and the second conductive element are printed on an inner side of the second protective insulator.

19. The movement-sensitive capacitive sensor of claim 18, wherein the first conductive element and the second conductive element comprise conductive ink printed on the inner side of the second protective insulator.

* * * * *